(12) United States Patent
Rustad (10) Patent No.: US 8,997,738 B2
(45) Date of Patent: Apr. 7, 2015

(54) DELIVERING DILUTED OXYGEN TO A PATIENT

(75) Inventor: Andre M. Rustad, Eltwanda, CA (US)

(73) Assignee: Carefusion 207, Inc., San Diego, CA (US)

(*) Notice: Subject to any disclaimer, the term of this patent is extended or adjusted under 35 U.S.C. 154(b) by 889 days.

(21) Appl. No.: 13/069,368

(22) Filed: Mar. 22, 2011

(65) Prior Publication Data

US 2012/0240924 A1 Sep. 27, 2012

(51) Int. Cl.
A62B 7/02 (2006.01)
A61M 16/12 (2006.01)
A61M 16/00 (2006.01)

(52) U.S. Cl.
CPC ............ *A61M 16/12* (2013.01); *A61M 16/127* (2014.02); *A61M 2016/003* (2013.01); *A61M 2202/0208* (2013.01)

(58) Field of Classification Search
USPC .......................... 128/200.11–200.24, 201.28, 128/202.28–203.11, 203.24–203.25, 128/204.18, 205.11, 205.13–205.17, 128/205.24, 207.12, 207.16; 251/206–209, 251/350; 138/46; 222/3; 239/590.3; 137/888, 890, 891; 417/179, 176, 180, 417/187, 182
See application file for complete search history.

(56) References Cited

U.S. PATENT DOCUMENTS

| 3,794,072 A * | 2/1974 | Diedrich et al. ............... 137/893 |
| 3,850,171 A * | 11/1974 | Ball et al. .................. 128/204.25 |
| 3,977,432 A | 8/1976 | Vidal |
| 3,995,625 A | 12/1976 | Needham |
| 4,036,253 A | 7/1977 | Fegan et al. |
| 5,372,129 A | 12/1994 | Ryder |
| 6,718,979 B1 | 4/2004 | Britt et al. |
| 2008/0066757 A1 * | 3/2008 | Stallard et al. ........... 128/205.25 |

FOREIGN PATENT DOCUMENTS

GB 2407043 A 4/2005

OTHER PUBLICATIONS

Jack Perkins, Scott Kahan, and Jack McCue, In a Page: Inpatient Medicine, 2007, Lippincott Williams & Wilkins, p. 215.*
Magda Mulder, Practical Guide for General Nursing Science, Part 2, 1999, Pearson South Africa, p. 535.*
Kelly A. Hubbell and Andrea Novak, Emergency Care Technician Curriculum, 2002, Jones & Bartlett Learning, p. 25.*
International Search Report and Written Opinion in PCT Application No. PCT/US2012/028821 dated Oct. 29, 2012 in 7 pages.
Extended European Search Report for Application No. 12760179.7/ Patent No. 2688628 dated Aug. 21, 2014.

* cited by examiner

*Primary Examiner* — Melanie Hand
*Assistant Examiner* — Ned T Heffner
(74) *Attorney, Agent, or Firm* — McDermott Will & Emery LP (57) ABSTRACT

A device for delivering diluted oxygen to a patient is provided. The device comprises a configurable oxygen delivery unit and multiple orifices in the configurable oxygen delivery unit. Each of the orifices has a size which pertains to a particular oxygen concentration. The configurable oxygen delivery unit is structured to enable selectively altering the oxygen concentration without requiring replacement of any components in a respiratory circuit.

51 Claims, 7 Drawing Sheets

Table 5

| Oxygen port | Diluter cavity | Orifice | Oxygen concentration and delivery rate | Low Delivery Rate | High Delivery Rate | Orifice size (inches) | Orifice size range (inches) | Drill Size (inches) |
|---|---|---|---|---|---|---|---|---|
| 1a | 4a | 3a | 24%-2 LPM | 2 LPM | 4 LPM | .0200 | .0100-.0400 | 76 |
| 1b | 4b | 3b | 28%-4 LPM | 4 LPM | 6 LPM | .0400 | .0200-.0550 | 60 |
| 1c | 4c | 3c | 31%-6 LPM | 6 LPM | 8 LPM | .0550 | .0400-.0760 | 54 |
| 1d | 4d | 3d | 35%-8 LPM | 8 LPM | 10 LPM | .0760 | .0550-.1065 | 48 |
| 1e | 4e | 3e | 40%-8 LPM | 8 LPM | 12 LPM | .1065 | .0760-.1270 | 36 |
| 1f | 4f | 3f | 45%-10 LPM | 10 LPM | 12 LPM | .1270 | .1065-.1719 | 1/8 |
| 1g | 4g | 3g | 50%-12 LPM | 12 LPM | 12 LPM | .1719 | .1270-.2000 | 11/64 |

DELIVERING DILUTED OXYGEN TO A PATIENT

FIELD OF THE INVENTION

The present technology relates generally to the respiratory field. More particularly, the present technology relates to delivering diluted oxygen to a patient.

BACKGROUND

Hospital patients suffering from cardiac or pulmonary problems, among other things, frequently need additional oxygen that can be provided, for example, using an oxygen diluter device. An oxygen diluter device is used for diluting the oxygen from an oxygen tank with room air and delivering the diluted oxygen to the patient at an accompanying flow rate. The oxygen tank usually provides 100% oxygen (also referred to herein as "pure oxygen"). Typically, a particular oxygen concentration is associated with a particular flow rate. For example, the flow rates that typically accompany 24% oxygen, 28% oxygen, 31% oxygen, 35% oxygen, and 50% oxygen respectively are 2 liters per minute (LPM) to 4 LPM, 4 LPM to 6 LPM, 6 LPM to 8 LPM, 8 LPM to 10 LPM, and 12 LPM, An oxygen concentration and its corresponding oxygen flow rate shall be referred to as an "oxygen concentration and delivery rate."

DESCRIPTION OF EMBODIMENTS

The drawings referred to in this description should not be understood as being drawn to scale unless specifically noted.

DESCRIPTION OF EMBODIMENTS

The discussion will begin with an overview of the general use of an oxygen diluter device. The discussion will then focus on embodiments of the present technology that provide delivery of diluted oxygen to a patient.

Overview

Conventional oxygen diluter devices include many components that require replacement, adjustment or being moved, among other things. For example, one kit for a first conventional oxygen diluter device includes 6 oxygen jet diluters, a hood, and a vinyl tip. Therefore, the kit for this first oxygen diluter device includes at least 8 components. The assembled oxygen diluter device includes at least 3 components—one of the 6 oxygen jet diluters, the hood, and the vinyl tip.

Each oxygen diluter jet for the first conventional kit delivers a single oxygen concentration and delivery rate for a given flow meter setting. For example, the 6 oxygen jet diluters respectively provide 24% oxygen at 2 LPM, 28% oxygen at 4 LPM, 31% oxygen at 6 LPM, 35% oxygen at 8 LPM, 40% oxygen at 8 LPM, and 50% oxygen at 12 LPM. Each of the oxygen jet diluters has one orifice that is different from the sizes of the orifices associated with the other oxygen jet diluters that enable each of the jet diluters to deliver a single oxygen concentration and delivery rate for a given flow meter setting. For example, the 24% oxygen at 2 LPM jet diluter has the smallest orifice, the 28% oxygen at 8 LPM jet diluter has the next smallest orifice and the 50% oxygen at 12 LPM jet diluter that has the largest orifice.

The oxygen concentration for a given orifice does not change. However, the delivery rate for a given orifice may be altered by changing the flow meter setting. For example, in the case of the oxygen jet diluter with the smallest orifice that corresponds to 24% oxygen, the delivery rate can be changed from 2 LPM to 4 LPM by changing the flow meter setting on the oxygen tank. However, the oxygen concentration will be 24% for both 2 LPM and 4 LPM with the oxygen jet diluter with the smallest orifice. In another example, in the case of the oxygen jet diluter with the next to smallest orifice that corresponds to 28% oxygen, the delivery rate can be changed from 4 LPM to 6 LPM by changing the flow meter setting on the oxygen tank. However, the oxygen concentration will be 28% for both 4 LPM and 6 LPM with the oxygen jet diluter with the next to smallest orifice.

The first conventional oxygen diluter device has to be disassembled and the oxygen jet diluter has to be replaced in order to change the oxygen concentration. More specifically, changing the oxygen concentration and delivery rate for this first conventional oxygen diluter device involves detaching the connector of the oxygen source, removing the humidifier cup, removing the oxygen jet diluter, inserting a new oxygen jet diluter, replacing the humidifier cup, reattaching the oxygen source's connector, and adjusting the flow meter at the oxygen source based on conventionally known flow meter charts, among other things.

Another kit for a second conventional oxygen diluter device includes two oxygen jet diluters, a sleeve that includes air entrainment windows, a humidifier cup and a vinyl tip. Therefore, the kit for this second oxygen diluter device includes at least 5 components. The second oxygen diluter device includes at least 4 components when assembled—one oxygen jet diluter, the sleeve, the hood and the vinyl tip.

One of the oxygen jet diluters in this second kit can be used to deliver 24% oxygen, 28% oxygen or 31% oxygen (also known as the "low concentration oxygen jet diluter"). The other oxygen jet diluter in this second kit can be used to deliver 30% oxygen, 35% oxygen, 40% oxygen, 45% oxygen, 50% oxygen or 55% oxygen (also known as the "medium concentration oxygen jet diluter"). The low concentration oxygen jet diluter has a single orifice and the medium concentration oxygen jet diluter also has a single orifice. The medium concentration oxygen jet diluter's orifice is larger than the low concentration oxygen jet diluter's orifice, thus, enabling the medium concentration oxygen jet diluter to deliver oxygen concentrations with higher levels of oxygen.

Changing the oxygen concentration and delivery rate includes many steps that involve disassembling components, moving components for example by rotating or adjusting components, reassembling components and possibly replacing components. For example, assume that hospital personnel want to change a patient's oxygen concentration and delivery rate from 24% oxygen at 2 LPM to 28% oxygen at 4 LPM. In this case, the change would involve removing the oxygen tube connector, removing the hood, pulling the sleeve out, adjusting the size of the entrainment windows by rotating the sleeve to a new position that corresponds to 28% oxygen at 4 LPM and pushing the sleeve down to lock it into the new position, replacing the hood, reattaching the oxygen tube connector and adjusting the flow meter at the oxygen source based on conventionally known flow meter charts, among other things.

The oxygen concentration for a given entrainment window size and a given oxygen jet diluter does not change. However, the delivery rate for a given entrainment window size and a given oxygen jet diluter may be altered by changing the flow meter setting. Continuing the above example, the oxygen delivery rate can be changed from 2 LPM to 4 LPM for the 24% oxygen by changing the flow meter setting based on conventionally known flow meter charts. Similarly, the oxygen delivery rate can be changed from 4 LPM to 6 LPM for the 28% oxygen by changing the flow meter setting based on conventionally known flow meter charts.

In another example, assume that hospital personnel want to change a patient's oxygen concentration and delivery rate from 31% oxygen at 6 LPM to 35% oxygen at 8 LPM. In this case, the change would involve removing the oxygen tube connector, removing the hood, removing the sleeve, removing the low concentration oxygen jet diluter, inserting the medium concentration oxygen jet diluter, adjusting the size of the entrainment windows by replacing, positioning and locking the sleeve to a position that corresponds to 35% oxygen concentration, replacing the hood, reconnecting the oxygen connector and adjusting the flow meter at the oxygen source based on conventionally known flow meter charts, among other things.

As can be seen, changing the oxygen concentrations includes adjusting the size of the air entrainment windows, among other things. The size of the air entrainment windows can be adjusted by adjusting the sleeve as discussed herein. For example, the oxygen concentration can be changed from 24% to 28% for the low concentration oxygen jet diluter by adjusting the sleeve causing the size of the air entrainment windows to change. Similarly, the oxygen concentration can be changed from 28% to 31% for the low concentration oxygen jet diluter by adjusting the sleeve as discussed herein. Further, the oxygen concentration can be changed from 30% to 35% for the medium concentration oxygen jet diluter by adjusting the sleeve causing the size of the air entrainment windows to change. Similarly, the oxygen concentration can be changed from 35% to 40%, 40% to 45%, and so on for the medium concentration oxygen jet diluter by adjusting the sleeve.

There are numerous disadvantages to the two conventional oxygen diluter devices. In a first example, changing the oxygen concentration for both of these conventional oxygen diluter devices takes approximately 5 minutes since various components associated with the kits are replaced, removed, inserted, pulled out, rotated, adjusted, pushed back in, or a combination thereof. In a second example, manufacturing the two conventional oxygen diluter devices is very expensive. Just one mold can cost as much as a quarter of a million dollars and a different mold is required for manufacturing each of the components. For example, 8 molds could be used for manufacturing the 8 components of the first kit and 5 molds could be used for manufacturing the 5 components in the second kit. In a third example, the components have to be disposed of in a biohazard dump regardless of whether components in a kit have been used by a patient because an oxygen diluter device can only be used for one patient and cannot be sterilized and subsequently used on another patient (also known as "single patient use"). If a patient only uses the 24% oxygen jet diluter of the first kit, all of the other unused jet diluters for 28%, 31%, 35%, 40% and 50% oxygen still have to be disposed of in the biohazard dump after the patient is discharged from the hospital.

According to one embodiment, a configurable oxygen delivery unit is provided that includes multiple orifices where each orifice has a size that pertains to a particular oxygen dilution rate. The configurable oxygen delivery unit has a structure that enables selectively altering the oxygen concentration without requiring replacement of any components in a respiratory circuit, according to one embodiment. For example, the configurable oxygen delivery unit includes multiple orifices where each of the orifices has a size that pertains to a particular oxygen dilution rate. The oxygen delivery unit can be configured, for example, by selecting one of the orifices. The oxygen concentration and delivery rate can be changed, according to one embodiment, by moving an oxygen tube's connector from one orifice to another orifice and adjusting the flow meter on an oxygen source. Further, adjusting the size of air entrainment windows is not required, since the oxygen concentration is changed by selecting a different orifice. Therefore, the oxygen concentration can be changed within a few seconds, according to various embodiments, instead of the typical 5 minutes for conventional diluter devices.

Further, according to another embodiment, the oxygen delivery unit consists of a single component. Therefore, only one mold is used to manufacture the configurable oxygen delivery unit, according to one embodiment, which results in a significant savings in the cost of creating molds and the time to manufacture the configurable oxygen delivery unit. Further savings in money and the environment can be realized because of the significant decrease in the number of components that will be disposed.

For the sake of simplicity, many of the embodiments are described in the context of a particular flow rate for a particular oxygen concentration. However, the flow rate can be altered for a particular oxygen concentration by changing the flow meter, as will become more evident.

Structure

Figure 1:
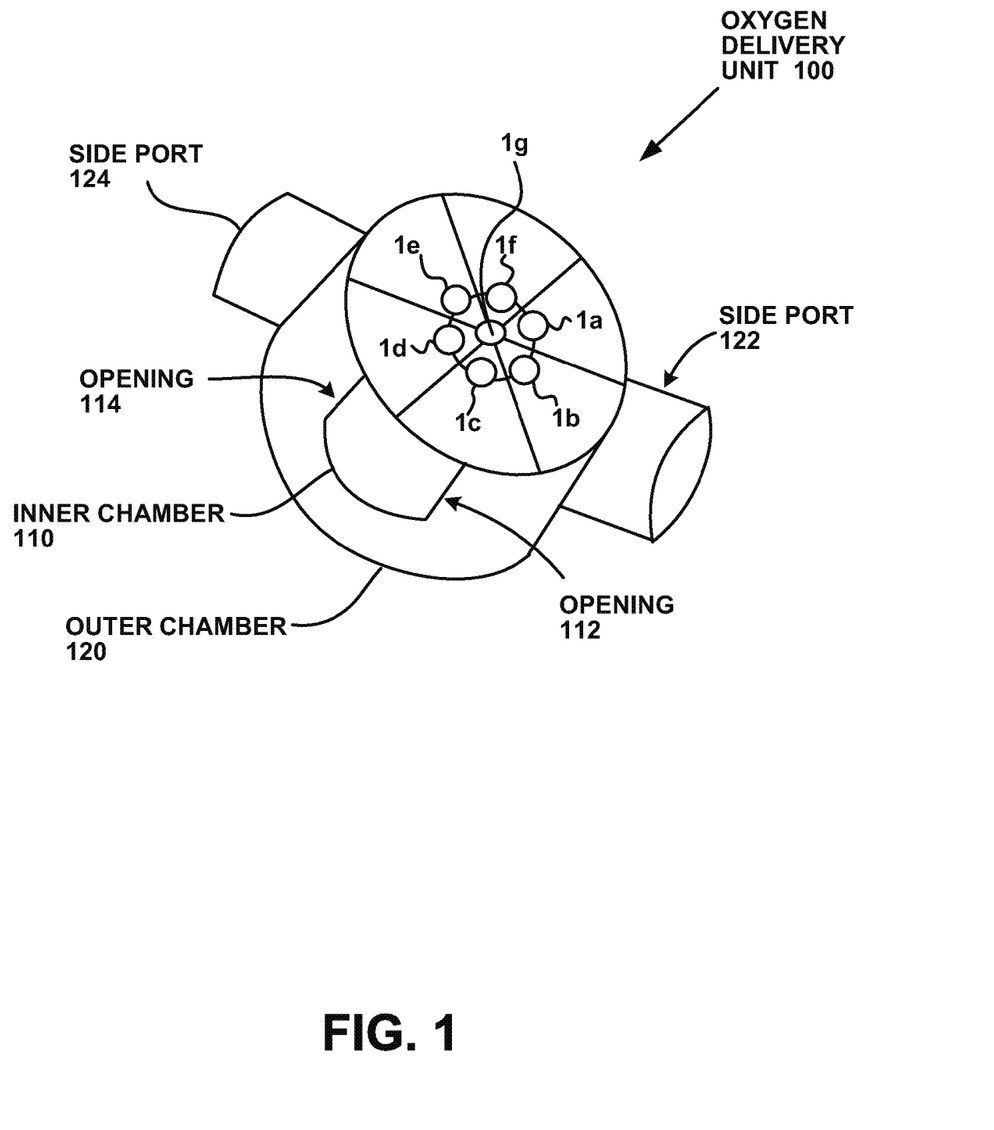
FIG. 1 is a perspective view of a configurable oxygen delivery unit, according to one embodiment.

FIG. 1 is a perspective view of a configurable oxygen delivery unit 100, according to one embodiment. As depicted in FIG. 1, the configurable oxygen delivery unit 100 includes an outer chamber 120, an inner chamber 110, 7 oxygen ports 1a-1g, a side port 122 in the outer chamber 120, a side port 124 in the outer chamber 120 and openings 112, 114 in the inner chamber 110. A window may be used instead of a port for one of the side ports 122 or 124, according to one embodiment. The delivery unit 100 is well suited for including additional or fewer features.

According to one embodiment, each of the oxygen ports 1a-1g can be used to deliver a different oxygen concentration. For example, port 1a is associated with 24% oxygen concentration at 2 LPM-4 LPM, port 1b is associated with 28% oxygen concentration at 4 LPM-6 LPM, port 1c is associated with 31% oxygen concentration at 6 LPM-8 LPM, port 1d is associated with 35% oxygen concentration at 8 LPM-10 LPM, port 1e is associated with 40% oxygen concentration at 8 LPM-12 LPM, port 1f is associated with 45% oxygen concentration at 10 LPM-12 LPM, and port 1g is associated with 50% oxygen concentration at 12 LPM, according to one embodiment. The oxygen concentration and delivery rate that is delivered to a patient can be changed by moving an oxygen tube connector 612 from one port 1a-1g to another port 1a-1g, as will become more evident.

The oxygen delivery rate for a particular port 1a-1g can be set anywhere in the specified ranges, for example, by adjusting the flow meter setting at the oxygen tank. More specifically, the oxygen delivery rate for port 1a can be changed to anywhere between 2 LPM to 4 LPM by adjusting the flow meter setting based on conventionally known flow meter charts. However, the oxygen concentration for port 1a will be 24% regardless of whether the oxygen deliver rate is 2 LPM or 4 LPM or anywhere in between 2 LPM and 4 LPM. For the sake of simplicity, many embodiments are described in the context of one oxygen delivery rate per oxygen concentration.

The inner chamber 110 and the outer chamber 120 each include two openings 112, 114, 122, 124. Room air can enter the inner chamber 110 through one or more of the inner and outer chamber openings 112, 114, 122, 124 or through the bottom of the outer chamber 120, the remaining unused ports (ports without an inserted oxygen connector) and mix with the 100% oxygen from the port 1a-1g that the oxygen connector 612 is inserted into. The mixing of room air with the 100% oxygen is known as "room air entrainment." Therefore, the inner chamber 110 is also referred to as an "air entrainment and delivery chamber 110" and the openings 112, 114 in the entrainment chamber 110 are also referred to as "air entrainment windows," according to one embodiment.

The openings in the outer chamber 120 are side ports 122, 124, according to one embodiment, for attaching an additional device. For example, a nebulizer, a second oxygen source, or a source of humidified air could be attached to one or both of the side ports 122, 124. The highest oxygen concentration that can be delivered using just a port, such as port 1g, is 50 percent. A side port 122, 124 allows hospital personnel to configure the device 100 to deliver an oxygen concentration that is higher than 50 percent to the patient. Since the side ports 122, 124 can be used for delivering humidified air, the outer chamber 120 is also referred to as a humidifier cup, according to one embodiment. The outer chamber 120 can also serve to prevent items, such as the bed sheets, from occluding the inner chamber's openings 112, 114. A window that room air enters can be used instead of a side port 122 or 124.

The device, according to one embodiment, has a height of approximately 1.777 inches. The outer chamber 120, according to one embodiment, has a height of approximately 1.250, a diameter at the top of approximately 1.835 inches and a diameter at the bottom of approximately 2.100 inches. The inner chamber 110, according to one embodiment, has an approximate height of 1.777 inches and has an outer diameter of 22 millimeters (mm). Therefore, according to one embodiment, there is approximately a 0.5270 inch difference between the heights of the inner chamber 110 and the outer chamber 120 with the inner chamber 110 being higher than the outer chamber 120.

According to one embodiment, the openings 112 and 114 have a width that is between 0.635 inches and 0.675 inches and a height that is between 0.200 inches and 0.320 inches. The openings 112 and 114, according to one embodiment, are approximately 0.675 inches wide and approximately 0.200 inches high. According to one embodiment, the side ports 122 and 124 are 22 millimeter (mm) ISO ports with an outer diameter of 22 millimeters (mm). However as any one of ordinary skill in the art would understand, embodiments are well suited to different shapes and sizes.

According to one embodiment, each of the oxygen ports 1a-1g is approximately the same size so that an oxygen tube connector 612 can be inserted into any of the oxygen ports 1a-1g. As will become more evident, a different sized orifice is associated with each of the oxygen ports 1a-1g so that different oxygen concentration and delivery rates can be delivered using each of the oxygen ports 1a-1g, according to one embodiment.

The sizes of various openings 112, 114, 122, 124, 1a-1g are fixed, according to one embodiment. The size of a fixed opening 112, 114, 122, 124, 1a-1g remains the same and, therefore, is not adjusted to be larger or smaller, according to one embodiment. Further, according to one embodiment, the size of each of the openings 112, 114 is fixed and, therefore, is not adjustable. According to another embodiment, the sizes of one or more openings 112, 114, 122, 124, 1a-1g are adjustable.

Although various embodiments have been described in the context of certain shapes and sizes for openings, such as oxygen ports 1a-1g, air entrainment windows 112, 114, and side ports 122, 124, embodiments are well suited to openings of different shapes and sizes. For example, the oxygen ports 1a-1g can be any shape or size that enables delivering different oxygen concentration and flow rates. In another example, the air entrainment windows 112, 114 can be any shape or size that enables entrainment of room air, among other things. In yet another example, the side ports 122, 124 can be any shape or size that enables receiving humidified air, nebulized medication, or additional oxygen, among other things.

Conventional tubing and the conventional coupling mechanisms of additional devices, such as nebulizers, humidifiers and various connectors, are circular with a 22 mm inner or outer diameter. Therefore, various embodiments have been described in the context of circular side ports 122, 124 with outer diameters of 22 mm and a circular inner chamber 110 with an inner diameter of 22 mms. However, various embodiments are well suited to the side ports 122, 124 and the inner chamber 110 having other shapes and size to accommodate, for example, different types of devices or tubing, A device for delivering diluted oxygen to a patient includes a single integral component, according to one embodiment. For example, the device can be made of one component, which may be the oxygen delivery unit. The outer chamber 120, the inner chamber 110, the top of the oxygen delivery unit 100 and the various openings 112, 114, 122, 124, 1a-1g can all be integral features of the oxygen deliver unit 100. Further, the oxygen delivery unit 100 can be made from a single mold.

Although various embodiments have been described in the context of a device for delivering diluted oxygen to a patient that includes a single component, such as a single integral oxygen delivery unit, various embodiments are well suited to an oxygen delivery unit that includes more than one component. For example, the inner chamber 110 may be a separate component from the rest of the oxygen delivery unit. In another example, as will become more evident, one or more of the labels that can be associated with the ports 1a-1g may be separate or integral to the oxygen delivery unit.

Figure 2:
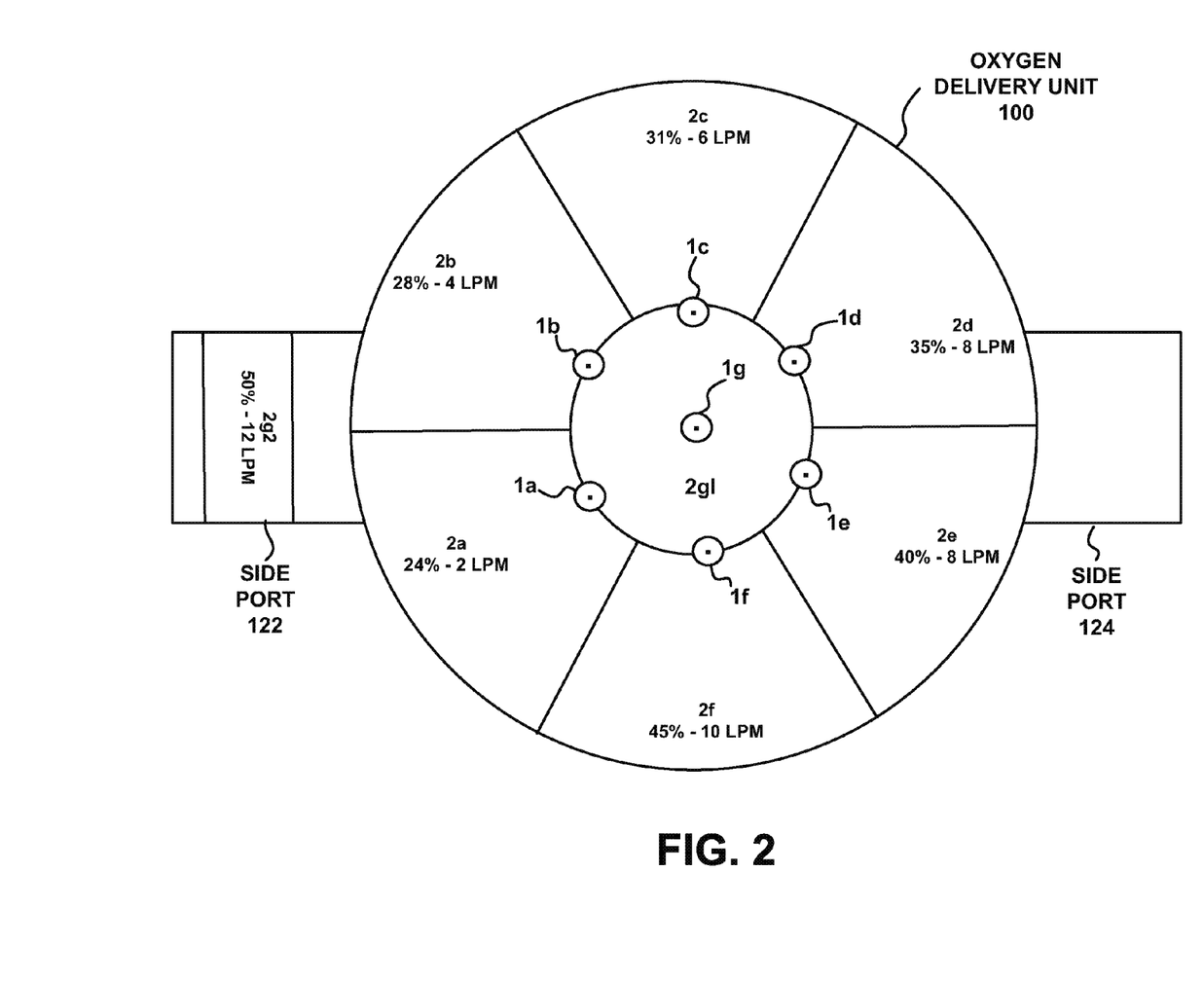
FIG. 2 is a top view of a configurable oxygen delivery unit, according to one embodiment.

FIG. 2 is a top view of a configurable oxygen delivery unit 100, according to one embodiment. The top view depicts the oxygen ports 1a-1g, labels 2a-2g, and the side port 122. However, the oxygen delivery unit 100 may include additional or fewer features.

The labels 2a-2g can be colored, according to one embodiment. For example, label 2a can be blue, label 2b can be yellow, label 2c can be white, label 2d can be green, label 2e can be pink, label 2f can be red, and labels 2g1 and 2g2 can be orange. However, other colors may be used for the labels.

According to one embodiment, the labels 2a-2g include writing indicating the oxygen concentration and the recommended flow rate or recommended flow rate range for the associated port. For example, the label 2a can include writing such as "24%-2 LPM." There may not be sufficient space for the center label 2g1 to include writing indicating the oxygen concentration and delivery rate for the center port 1g. Therefore, according to one embodiment, the label 2g1 in the center is colored but does not include writing. An additional label 2g2 may be placed on one of the side ports 122, 124 with writing, such as "50%-12 LPM," that indicates the oxygen concentration and delivery rate associated with the center port 1g. The additional label 2g2 on the side port 122, 124 may be the same color as the label 2g1 in the center.

The labels 2a-2g may be attached to the oxygen delivery unit 100, for example, by gluing the labels 2a-2g on the unit 100. Alternatively, the labels 2a-2g may be engraved on the oxygen delivery unit 100. The engraving may be high lighted. Further, some of the labels 2a-2g may be attached to the oxygen delivery unit 100 while others are engraved. For example, labels 2a-2f and 2g1 may be attached while label 2g2 may be engraved.

Figure 3:
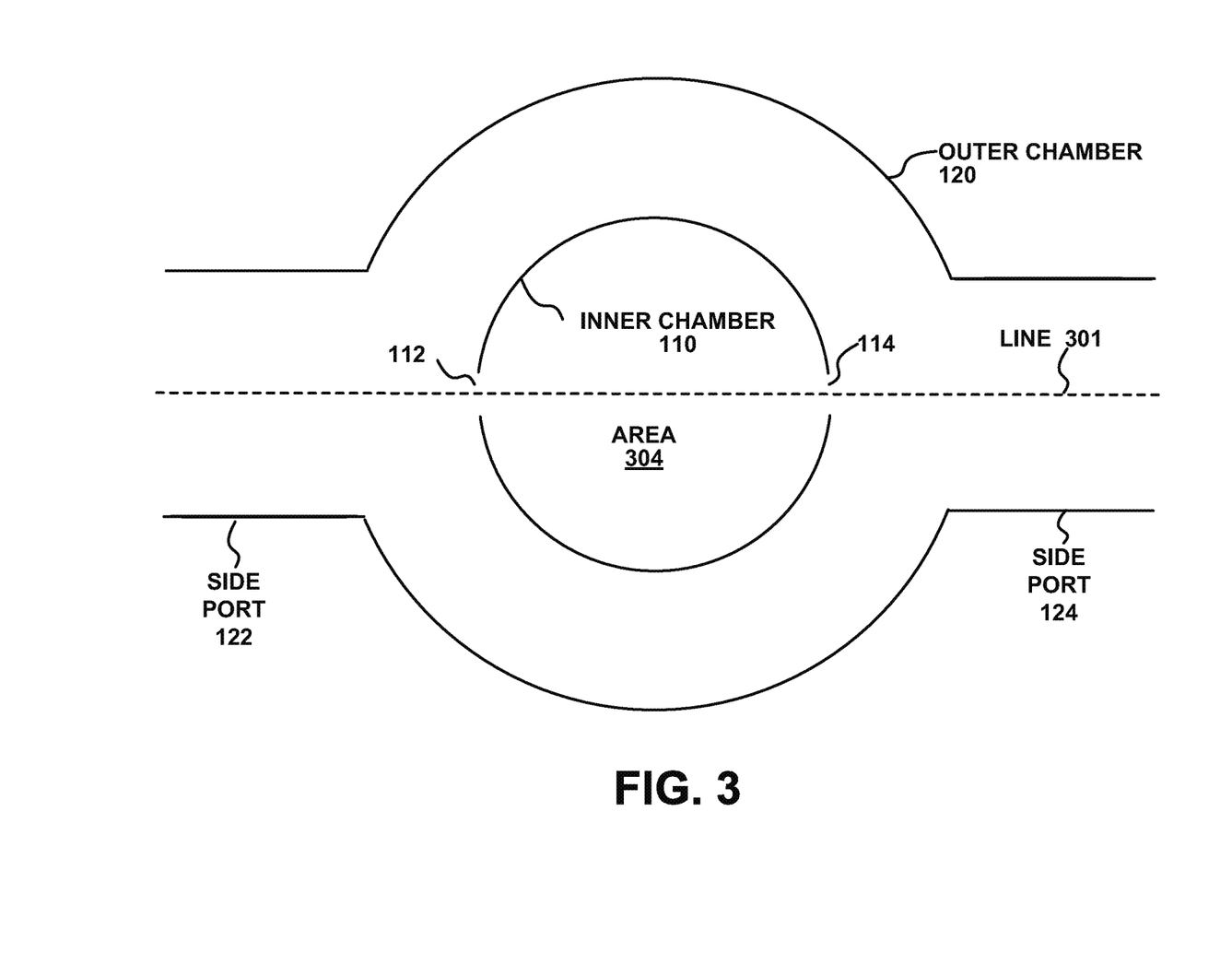
FIG. 3 is a top cross sectional view of a configurable oxygen delivery unit, according to one embodiment.

FIG. 3 is a top cross sectional view of a configurable oxygen delivery unit 100, according to one embodiment. The top cross section of the oxygen delivery unit 100 depicts the outer chamber 120, the inner chamber 110, the side ports 122, 124 in the outer chamber 120 and the two openings 112, 114 in the inner chamber 110. According to one embodiment, the outer chamber's openings 122, 124 and the inner chamber's openings 112, 114 are oriented with respect to each other along an imaginary straight line 301 that goes through the center of the oxygen delivery unit 100.

Although various embodiments have been described in the context of the openings 122, 124, 122, 124 in the inner chamber 110 and outer chamber 120 being aligned along an imaginary straight line 301, embodiments are well suited to other orientations of the openings 122, 124, 122, 124 that provide for air entrainment, receiving nebulized medication and receiving humidified air, among other things. Further, embodiments are well suited to fewer or additional openings.

As depicted in FIGS. 1 and 2, the oxygen delivery unit 100 includes 7 oxygen ports. According to one embodiment, an oxygen delivery unit 100 can include as many oxygen ports 1a-1g as can be accommodated by the area 304 formed inside of the inner chamber 110 (FIG. 3). The oxygen delivery unit 100 can include fewer than 7 oxygen ports. For example, the oxygen delivery unit 100 can include 2-6 oxygen ports instead of 7 oxygen ports.

Figure 4:
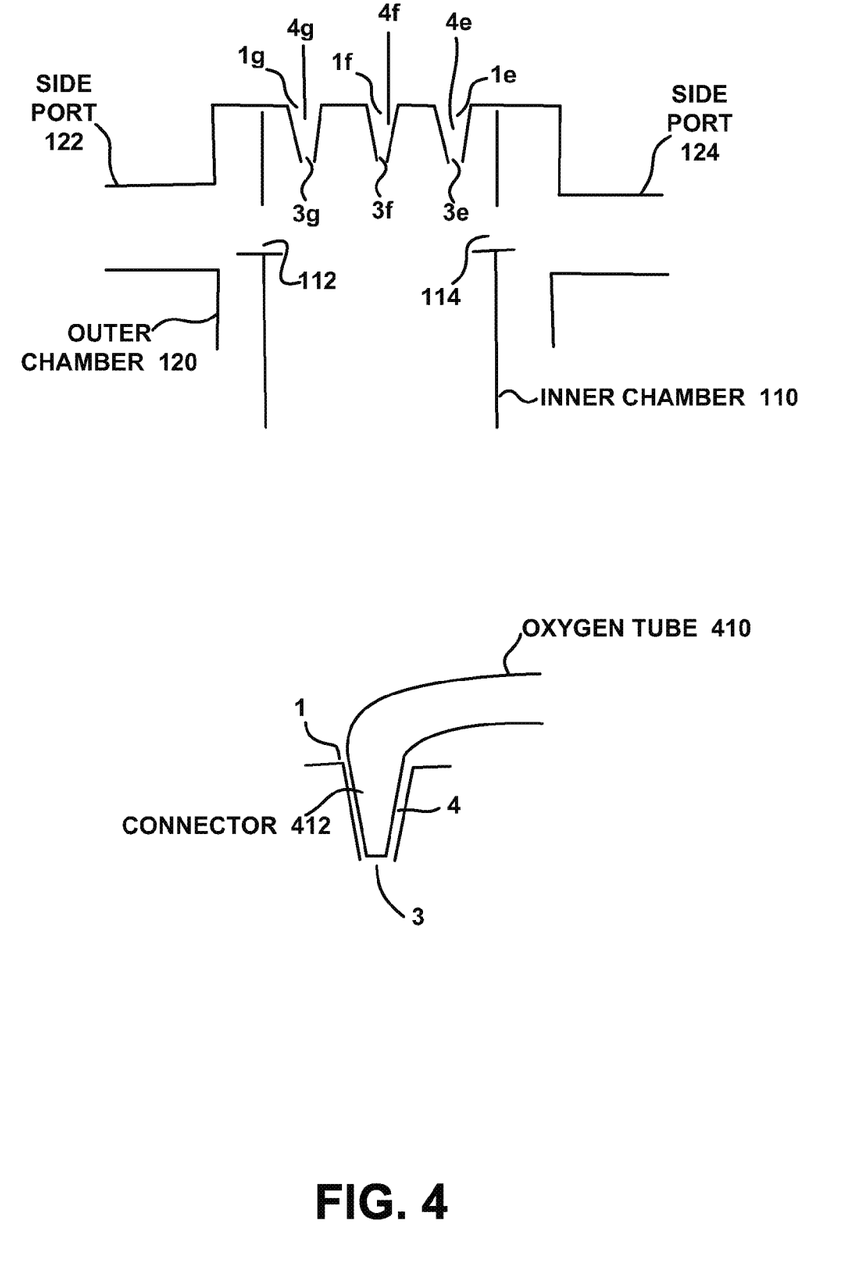
FIG. 4 is a side cross sectional view of an oxygen delivery unit, according to one embodiment.

FIG. 4 is a side cross sectional view of an oxygen delivery unit 100, according to one embodiment. The side cross section depicts the inner chamber 110, the outer chamber 120, oxygen ports 1a, 1f, 1e, oxygen diluter cavities 4a, 4f, 4e, orifices 3a, 3f, 3e, and the openings 112, 114, 122, 124 in the inner and outer chambers 110, 120. Since FIG. 4 depicts a side cross section, subsets of the oxygen ports, oxygen diluter cavities, and orifices are depicted.

FIG. 4 also depicts an enlarged view of an oxygen diluter cavity 4, according to one embodiment. An oxygen port 1 is at the top of each of the cavities 4 and an orifice 3 is at the bottom of each cavity 4, according to one embodiment. The oxygen diluter cavities 4 are configured to accommodate an oxygen tube connector 412 of an oxygen tube 410, according to one embodiment. For example, the ports 1a-1g may be large enough for the oxygen tube connector 412 to be inserted into the cavities 4. Conventionally, oxygen tube connectors 412 are circular and tapered. Therefore, a circular port 1 may be at the top of the cavity 4 and a cavity 4 may have tapered walls to accommodate a tapered oxygen connector 412. A cavity 4 may have a length that accommodates the length of the oxygen connector 412.

Although various embodiments are described in the context of circular ports 1a-1g and tapered cavities 4 to accommodate conventional oxygen tube connectors 412, various embodiments are well suited for ports 1a-1g and cavities 4 of other shapes and sizes, for example, to accommodate new types of oxygen tube connectors. More specifically, although various embodiments are described in the context of female diluter cavities that receive male oxygen tube connectors, embodiments are well suited for male diluter cavities that can be inserted into female oxygen tube connectors. Therefore, the term "port" shall be used to refer to both female type ports that a male oxygen tube connector can be inserted into and male type ports that can be inserted into a female oxygen tube connector.

Figure 5:
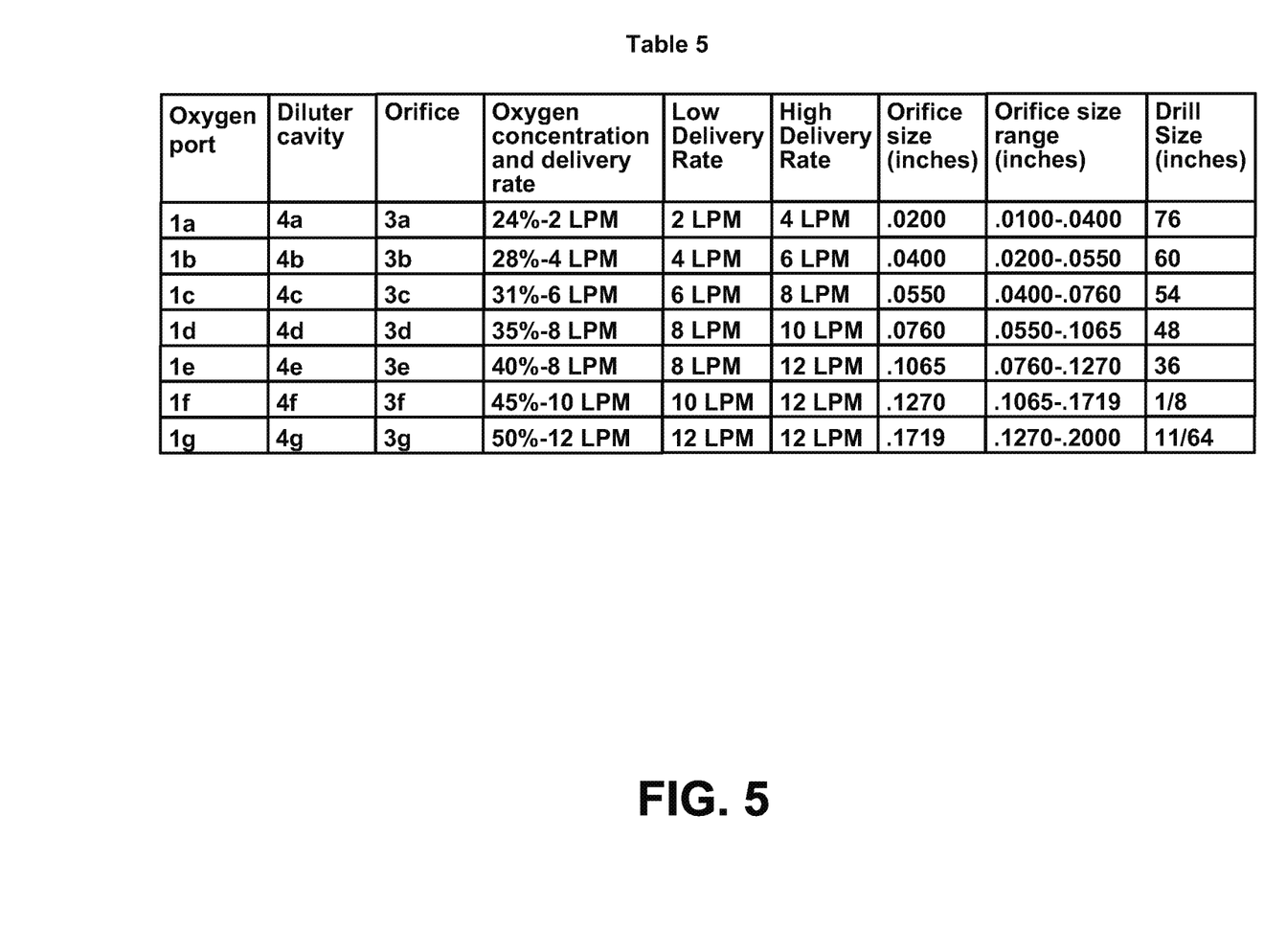
FIG. 5 depicts a table with reference numbers for the oxygen ports, the oxygen diluter cavities, the orifices, the corresponding oxygen concentration, corresponding low oxygen delivery rates, corresponding high oxygen delivery rates, approximate orifice sizes, approximate orifice size ranges, and approximate drill sizes that result in the corresponding orifice sizes, according to one embodiment.

FIG. 5 depicts a table with reference numbers for the oxygen ports, the oxygen diluter cavities, the orifices, the corresponding oxygen concentration, corresponding low oxygen delivery rates, corresponding high oxygen delivery rates, approximate orifice sizes, approximate orifice size ranges, and approximate drill sizes that result in the corresponding orifice sizes, according to one embodiment. The sizes depicted in FIG. 5 are diameters, according to one embodiment.

As depicted in Table 5, 24% oxygen at 2 LPM-4 LPM for port 1a is associated with an orifice 3a that has an approximate size of 0.0200 inch, 28% oxygen at 4 LPM-6 LPM for port 1b is associated with an orifice 3b that has an approximate size of 0.0400 inch, 31% oxygen at 6 LPM-8 LPM for port 1c is associated with an orifice 3c that has an approximate size of 0.0550 inch, 35% oxygen at 8 LPM-10 LPM for port 1d is associated with an orifice 3d that has an approximate size of 0.0760 inch, 40% oxygen at 8 LPM-12 LPM for port 1e is associated with an orifice 3e that has an approximate size of 0.1065 inch, 45% oxygen at 10 LPM-12 LPM for port 1f is associated with an orifice 3f that has an approximate size of 0.1270 inch, and 50% oxygen at 12 LPM for port 1g is associated with an orifice 3g that has an approximate size of 0.1719 inch, according to various embodiments. Therefore, each of the orifices 3a-3g has a size which pertains to a particular oxygen concentration, according to one embodiment.

The oxygen delivery rate for a particular orifice 3a-3g can be set anywhere in the specified ranges by adjusting the flow meter setting at the oxygen tank based on conventionally known flow meter charts, for example. More specifically, the oxygen delivery rate for orifice 1a can be changed to anywhere between 2 LPM to 4 LPM by adjusting the flow meter setting. However, the oxygen concentration for orifice 1a will be 24% regardless of whether the oxygen deliver rate is 2 LPM or 4 LPM or anywhere in between 2 LPM and 4 LPM. For the sake of simplicity, many embodiments are described in the context of one oxygen delivery rate per oxygen concentration.

According to one embodiment, the size of the respective orifices 3a-3g can have an approximate diameter in the respective ranges of 0.0100-0.0400, 0.0200-0.0550, 0.0400-0.0760, 0.0550-0.1065, 0.0760-0.1270, 0.1065-0.1719, and 0.1270-0.2000 inch, as depicted in FIG. 5. According to one embodiment, the respective drill sizes 76, 60, 54, 48, 36, ⅛ and ¹¹⁄₆₄ can be used to drill respective orifice sizes of 0.0200, 0.0400, 0.0550, 0.0760, 0.1067, 0.1270 and 0.1719 inch for orifices 1a-1g.

The size of an orifice 3a-3g determines the velocity of the air passing through the orifice 3a-3g, according to one embodiment. Room air can be entrained with the oxygen from an oxygen source by the shear forces at the boundary of jet flow. Therefore, the smaller the orifice 3a-3g's size, the greater the velocity of the oxygen and the more room air that is entrained resulting in a lower concentration of oxygen. For example, orifice 3a results in the highest velocity and the lowest oxygen concentration since it is the smallest and orifice 3g results in the lowest velocity and the highest oxygen concentration since it is the largest.

The amount of room air that is entrained depends on the size of an orifice 3a-3g and the size of the air entrainment windows 112, 114, according to one embodiment. According to one embodiment, the size of the air entrainment windows 112, 114 is maximized so that the amount of room air entrained depends only on the size of the orifice 3a-3g. Further, by maximizing the size of the air entrainment windows 112, 114, the air that is entrained through the unused ports becomes negligible, according to one embodiment.

Although various embodiments have been described in the context of air entrainment windows and orifices with certain sizes and dimensions, embodiments are well suited for orifices and air entrainment windows that have different sizes and shape to achieve desired oxygen concentration and flow rates. Although various embodiments are described in the context of oxygen concentration and flow rates depicted in FIG. 5, embodiments are well suited to other oxygen concentration and flow rates if desired.

According to one embodiment, the oxygen concentration and delivery rate can be changed without adjusting the size of air entrainment windows 112, 114. For example, the oxygen concentration can be changed from a first concentration to a second concentration by removing the oxygen tube connector 612 from a first port 1a-1g with an orifice size that results in the first concentration and inserting the oxygen tube connector 612 into a second port 1a-1g with an orifice size that results in the second concentration. More specifically, the oxygen concentration and delivery rate could be changed from 24% at 2 LPM to 28% at 4 LPM, for example, by removing an oxygen tube connector from port 1a and then inserting it into port 1b and adjusting the meter flow on the oxygen tank to a rate that corresponds to 28% at 4 LPM. Therefore, the oxygen concentration and delivery rate can be altered without adjusting the size of the air entrainment windows 112, 114.

Although various embodiments have been described in the context of each of the oxygen ports 1a-1g (FIG. 1) being used for a corresponding oxygen concentration and delivery rate, embodiments are well suited to using a port on the top of the unit 100 for other purposes. For example, instead of associating a fixed orifice 3a-3g with each of the ports 1a-1g, one of the ports 1a-1g could be used instead for delivering nebulized medication or humidified air, among other things.

There has been a long felt need for an oxygen delivery unit 100 that reduces the amount of time it takes to change the oxygen concentration, which reduces the number of components that are disposed, that reduces the number of molds required to manufacture the oxygen deliver unit, and that reduces the number of components that are manufactured. However, it has been conventionally believed that multiple orifices 3a-3g (FIG. 5) cannot be associated with a configurable oxygen delivery unit 100 (FIG. 1) where each of the orifices 3a-3g has a size which pertains to a particular oxygen concentration (FIG. 5). For example, it has been conventionally believed that if an oxygen delivery unit included multiple orifices, too much of the air would escape through the air entrainment windows. However, according to one embodiment, this conventionally believed problem has been proven incorrect, for example, by positioning the largest orifice 3g (FIGS. 2 and 5), which results in the lowest velocity, in the center and the smaller orifices 3a-3f (FIGS. 2 and 5), which result in higher velocities, on the outside nearer the air entrainment windows 112, 114 (FIGS. 1 and 3), among other things. Therefore, the oxygen delivery unit 100 (FIGS. 1-4), according to various embodiments, has addressed several long felt needs and provided unexpected results that ones of ordinary skill in the art have not envisioned.

Figure 6:
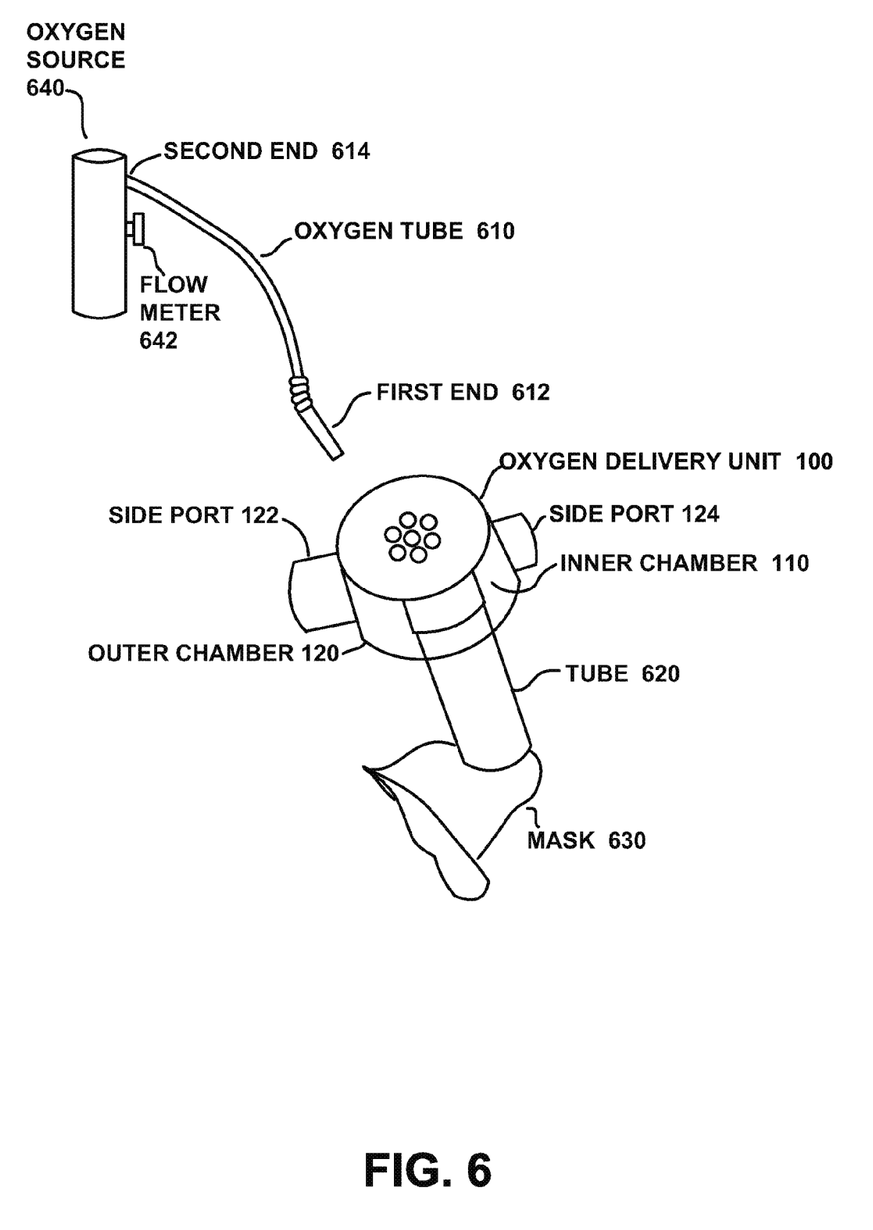
FIG. 6 is a perspective view of a respiratory circuit, according to another embodiment.

FIG. 6 is a perspective view of a respiratory circuit 600, according to another embodiment. A respiratory circuit, according to one embodiment includes the components that are used for delivering oxygen from an oxygen source to a patient through a mask, according to one embodiment. For example, as depicted in FIG. 6, a respiratory circuit can include the oxygen source 640, the oxygen tube 610, the configurable oxygen delivery unit 100, the flexible tube 620 and the mask 630. However, the respiratory circuit 600 is well suited for including additional or fewer features. For example, the respiratory circuit 600 may also include an additional device that is coupled to a side port 122, 124, as described herein.

An oxygen tube 610 can be used to provide oxygen to the configurable delivery unit 100 from an oxygen source 640. For example, one end 614 of the oxygen tube 610 can be connected to an oxygen source 640, such as an oxygen tank that provides 100% oxygen. The other end 612 of the oxygen tube 610 can be inserted into one of the oxygen ports 1a-1g of the oxygen delivery unit 100. The oxygen delivery unit 100 is coupled to a tube 620, for example, by press fitting the tube 620 into the inner chamber 110 of the oxygen delivery unit 100. The tube 620 is coupled with a face mask 630.

According to one embodiment, the tube 620 is flexible so that it can be bent allowing the patient more freedom of motion. The flexible tube 620 may be made of corrugated or ribbed plastic, among other things. Conventionally, the outer diameter of the tube 620 is 22 mm. Therefore, various embodiments have been described in the context of a circular inner chamber 110 with an inner diameter of 22 mm that is compatible with a conventional circular tube 620 that has an outer diameter of 22 mm. However, various embodiments are well suited for an inner chamber 110 having other dimensions or shape, for example, to couple with new types of tubing.

An additional oxygen source, a nebulizer or a device that provides humidified air can be coupled to the unit 100 through a side port 122, 124. Typically, the humidity in room air is sufficient to prevent the lungs from drying out for flow rates of 4 LPM and below. Therefore, if the flow rate of the selected oxygen concentration and delivery rate is sufficiently low, the side port 122, 124 might not be coupled with another device so that room air instead of humidified air or nebulized medication enters through the side port 122, 124.

Method for Delivering Diluted Oxygen

Figure 7:
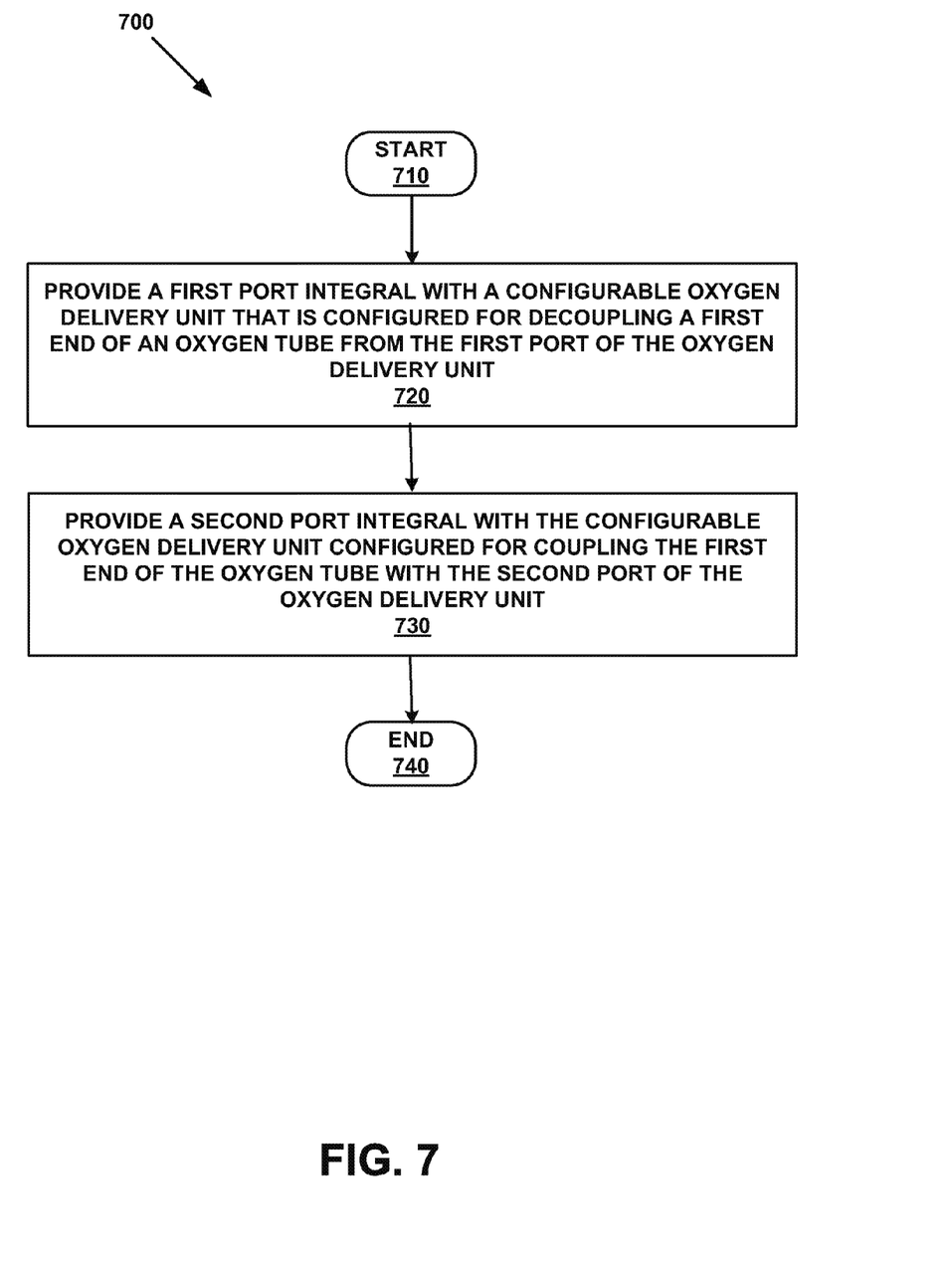
FIG. 7 is a flow chart for a method of delivering diluted oxygen to a patient, according to one embodiment.

FIG. 7 is a flow chart for a method of delivering diluted oxygen to a patient, according to one embodiment. The method may include additional or fewer operations than what are depicted in FIG. 7.

The following description of flowchart 700 shall refer to FIGS. 1 and 6. The following description of flowchart 700 assumes that the hospital personnel want to change the oxygen concentration and delivery rate from 24% oxygen concentration at 2 LPM to 28% oxygen concentration at 4 LPM. In preparation for the description of flowchart 600, assume that the first end 612 of the oxygen tube 610 is inserted into oxygen port 1a and the second end 614 of the oxygen tube 610 is connected to a source of oxygen 640, such as an oxygen tank. An orifice with an approximate diameter of 0.0200 inch is associated with oxygen port 1a, according to one embodiment, as depicted in FIG. 5. The orifice size associated with port 1a will result in an oxygen concentration and delivery rate of 24% oxygen at 2 LPM provided that an appropriate adjustment has been made to oxygen source 640's flow meter 642. More specifically, there are conventionally known flow meter charts that hospital personal can look up the oxygen concentration and delivery rate of 24% oxygen at 2 LPM to determine how to set the flow meter 642. Therefore, the patient receives 24% oxygen at 2 LPM when the oxygen tube 610 is inserted into oxygen port 1a and a corresponding adjustment has been made to the flow meter 642.

Although the oxygen delivery rate can be adjusted for a given oxygen concentration by changing the flow meter setting, as discussed herein, for the sake of simplicity, the following illustration shall assume one flow rate per oxygen concentration.

The method begins at 710.

At 720, a first port integral with a configurable oxygen delivery unit that is configured for decoupling a first end of an oxygen tube from the first port of the oxygen delivery unit is provided. In this illustration, the first port is port 1a. The first port 1a is integral with the oxygen delivery unit 100. The first port 1a is configured to accommodate an oxygen tube connector 612 so that the oxygen tube connector 612 can be coupled or decoupled from the first port 1a.

If hospital personnel want to change the oxygen concentration delivery rate, they can remove the oxygen tube connector 612 from the first port 1a in preparation for inserting the oxygen tube connector 612 into a different port.

At 730, a second port integral with the configurable oxygen delivery unit configured for coupling the first end of the oxygen tube with the second port of the oxygen delivery unit is provided. In this illustration, the second port is port 1b. The second port 1b is integral with the oxygen delivery unit 100. The second port 1b is configured to accommodate an oxygen tube connector 612 so that the oxygen tube connector 612 can be coupled or decoupled from the second port 1b.

A different oxygen concentration and delivery rate is associated with each of the oxygen ports 1a-1g. For example, 24% oxygen concentration at 2 LPM can be delivered to a patient when the oxygen tube connector 612 is inserted into oxygen port 1a and 28% oxygen concentration at 4 LPM can be delivered to the patient when the oxygen tube connector 612 is inserted into oxygen port 1b so that a different oxygen concentration and delivery rate is delivered for each of the oxygen ports 1a and 1b.

This illustration assumes that the hospital personnel want to change the oxygen concentration and delivery rate from 24% oxygen concentration at 2 LPM to 28% oxygen concentration at 4 LPM. An orifice with a diameter of approximately 0.0400 inches is associated with oxygen port 1b, according to one embodiment, as depicted in FIG. 5. This orifice 1b's size will result in an oxygen concentration and delivery rate of 28% oxygen concentration at 4 LPM provided an appropriate adjustment has been made to the oxygen source's flow meter 642 based on the conventionally known flow meter charts, as discussed herein. Therefore, the patient receives 28% oxygen concentration at 4 LPM when the oxygen tube 610 is inserted into oxygen port 1b and a corresponding adjustment has been made to the flow meter 642.

The configurable oxygen delivery unit 100 is structured to enable selectively altering the oxygen concentration and delivery rate without requiring replacement of any components 640, 610, 100, 620, 630 in a respiratory circuit 600 (FIG. 6). For example, the oxygen delivery unit 100 is structured to include an orifice with an approximate diameter of 0.0200 inch, which results in 24% oxygen at 2 LPM, and to include an orifice with an approximate diameter of 0.0400 inch, which results in 28% oxygen at 4 LPM, associated respectively with ports 1a and 1b. The oxygen concentration and delivery rate is selectively altered in this illustration by removing the oxygen tube connector 612 from port 1a at 720 and inserting the oxygen tube connector 612 into port 1b at 730 provided appropriate adjustments are made to oxygen source's flow meter 642, as discussed herein. Therefore, the oxygen concentration and delivery rate can be changed without requiring replacement of any components 640, 610, 100, 620, 630 in the respiratory circuit 600 (FIG. 6), according to one embodiment.

Further, the oxygen concentration and delivery rate can be changed without adjusting the size of air entrainment windows 112, 114, according to one embodiment. For example, the oxygen concentration and delivery rate can be changed from a first concentration and rate to a second concentration and rate by removing the oxygen tube connector 612 from a first port 1a-1g with an orifice size that results in the first concentration and rate and inserting the oxygen tube connector 612 into a second port 1a-1g with an orifice size that results in the second concentration and rate. Therefore, the oxygen concentration and delivery rate can be altered by selecting a different orifice without adjusting the size of the air entrainment windows 112, 114.

The method ends at 740.

Although the above illustration of flowchart 700 used oxygen port 1a as the first port and oxygen port 1b as the second port, various embodiments are well suited for any oxygen port 1a-1g to be the first port or second port.

Additional Device Embodiments

In one embodiment, in the above illustration of flowchart 700, orifice 3a is an example of a first-oxygen-concentration-delivery-component configured to delivery a first oxygen concentration to a patient and orifice 3b is an example of a second-oxygen-concentration-delivery component configured to deliver a second oxygen concentration to the patient. However, various embodiments are well suited for any orifice to be first-oxygen-concentration-delivery-component and any oxygen port to be a second-oxygen-concentration-delivery-component.

According to various embodiments, the components configured to deliver oxygen concentration can also include a port 1a-1g and a cavity 4a-4g. Ports 1a-1g are examples of oxygen-tube-connector-to-device-coupling-component configured to couple an oxygen tube connector to the device 100. An air entrainment and delivery chamber 110 is an example of a room-air-entrainment-component configured to entrain room air into oxygen that the device 100 receives, for example, from an oxygen source. An outer chamber 120 is an example of a air-entrainment-windows-occlusion-prevention-component configured to prevent occlusion of one or more of the air entrainment windows. Openings 122 and 124 in the outer chamber 120 are examples of room-air-entrance-component configured to allow room air to enter the air-entrainment-windows-occlusion-prevention-component.

Side ports 122, 124 are examples of an additional-device-coupling-component configured to couple an additional device with the device 100, an additional-oxygen-receiving-component, a humidified-air-receiving-component configured to receive humidified air and a nebulized-medication-receiving-component configured to receive nebulized medication. According to various embodiments, there are other functions and structures that are described herein that provide support for yet other means.

CONCLUSION

A configurable oxygen delivery unit is provided that includes multiple orifices where each orifice has a size that pertains to a particular oxygen dilution rate, according to one embodiment. The configurable oxygen delivery unit has a structure that enables selectively altering the oxygen concentration without requiring replacement of any components in a respiratory circuit, according to one embodiment. For example, the configurable oxygen delivery unit includes multiple orifices where each of the orifices has a size that pertains to a particular oxygen dilution rate. The oxygen delivery unit can be configured, for example, by selecting one of the orifices. The oxygen concentration can be changed, according to one embodiment, by moving an oxygen tube connector from one orifice to another orifice and adjusting the flow meter on an oxygen source. Therefore, the oxygen concentration can be changed within a few seconds, according to various embodiments, instead of the typical 5 minutes for conventional diluter devices.

According to one embodiment, the oxygen concentration can be changed without adjusting the size of air entrainment windows. For example, the oxygen concentration can be changed from a first concentration to a second concentration by removing the oxygen tube connector from a first port with an orifice size that results in the first concentration and inserting the oxygen tube connector into a second port with an orifice size that results in the second concentration.

Therefore, the oxygen concentration can be altered by selecting a different orifice without adjusting the size of the air entrainment windows.

Further, according to another embodiment, the oxygen delivery unit consists of a single component. Therefore, only one mold is used to manufacture the configurable oxygen delivery unit, according to one embodiment, which results in a significant savings in the cost of creating molds and the time to manufacture the configurable oxygen delivery unit. Further savings in money and for the environment can be realized because of the significant decrease in the number of components that will be disposed of at a biohazard dump.

Since the oxygen concentration can be changed, according to various embodiments, by moving an oxygen tube connector from one oxygen port to another oxygen port, the oxygen concentration can be changed without requiring the oxygen delivery unit to include additional components besides the single component that forms the oxygen delivery unit, without requiring the oxygen delivery unit to include moveable components, without requiring the oxygen delivery unit to include adjustable components, and without requiring the oxygen delivery unit to include replaceable components, according to various embodiments.

There has been a long felt need for an oxygen delivery unit that enables changing oxygen concentration without requiring replacement of any components in a respiratory circuit. There has been a long felt need for an oxygen delivery unit that reduces the number of molds, the number of components manufactured and the number of components that are disposed of in a biohazard dump. There has been a long felt need for an oxygen delivery unit that reduces the amount of time it takes to change the oxygen concentration. However, it has been conventionally believed that multiple orifices 3a-3g (FIG. 5) cannot be associated with a configurable oxygen delivery unit 100 (FIG. 1) where each of the orifices 3a-3g has a size which pertains to a particular oxygen concentration (FIG. 5). For example, it has been conventionally believed that if an oxygen delivery unit included multiple orifices, too much of the air would escape through the air entrainment windows. However, according to one embodiment, this conventionally believed problem has been proven incorrect, for example, by positioning the largest orifice 3g (FIGS. 2 and 5), which results in the lowest velocity, in the center and the smaller orifices 3a-3f (FIGS. 2 and 5), which result in higher velocities, on the outside nearer the air entrainment windows 112, 114 (FIGS. 1 and 3), among other things. Therefore, the oxygen delivery unit 100 (FIGS. 1-4), according to various embodiments, has addressed several long felt needs and provided unexpected results that ones of ordinary skill in the art have not envisioned.

By providing an oxygen delivery unit that is simpler than conventional oxygen delivery units, diluted oxygen can be provided to a patient more easily while transporting the patient, for example, in an ambulance. For example, an oxygen delivery unit is simpler than conventional delivery units, according to various embodiments, because it does not require replacement of any components in the respiratory circuit, among other things, as described herein.

Examples of the subject matter are thus described. Although the subject matter has been described in a language specific to structural features and/or methodological acts, it is to be understood that the subject matter defined in the appended claims is not necessarily limited to the specific features or acts described above. Rather, the specific features and acts described above are disclosed as example forms of implementing the claims.

Various embodiments have been described in various combinations. However, any two or more embodiments may be combined. Further, any embodiment may be used separately from any other embodiment. Features, structures, or characteristics of any embodiment may be combined in any suitable manner with one or more other features, structures, or characteristics.

What is claimed is:

1. A device for delivering diluted oxygen to a patient, the device comprising:
   a configurable oxygen delivery unit; and
   multiple orifices in the configurable oxygen delivery unit, each orifice (i) forming a jet flow of oxygen entering the device, and (ii) having a size that pertains to a particular oxygen concentration, wherein the size of each orifice determines a velocity of oxygen, at a predetermined flow rate, entering the device through the respective orifice, and wherein the velocity of oxygen is selected to entrain room air to achieve a predetermined oxygen concentration within the device,
   wherein the configurable oxygen delivery unit is structured to enable selectively altering the oxygen concentration within the device by fluidly coupling an oxygen tube connector with an orifice pertaining to an particular oxygen concentration.

2. The device of claim 1, wherein the orifices include a first orifice that is the largest orifice and a second orifice that is smaller than the first orifice and wherein the first orifice is located in the center of the configurable oxygen delivery unit and the second orifice is located off center of the configurable oxygen delivery unit.

3. The device of claim 1, wherein the orifices include a first orifice that is the largest orifice and other orifices that are smaller than the first orifice and wherein the first orifice is located in the center of the configurable oxygen delivery unit and the other orifices are located around the first orifice.

4. The device of claim 1, wherein the orifices have sizes selected from a group of ranges consisting of 0.0100-0.0400 inch, 0.0200-0.0550 inch, 0.0400-0.0760 inch, 0.0550-0.1065 inch, 0.0760-0.1270 inch, 0.1065-0.1719 inch, and 0.1270-0.2000 inch.

5. The device of claim 1, wherein the orifices have approximate sizes selected from a group consisting of approximately 0.0200 inch, 0.0400 inch, 0.0550 inch, 0.0760 inch, 0.1065 inch, 0.1270 inch, and 0.1719 inch.

6. The device of claim 1, wherein the sizes of the orifices are fixed.

7. The device of claim 1, wherein each orifice comprises a port that is located on the top of the oxygen delivery unit, each port configured to receive an oxygen tube connector.

8. The device of claim 7, wherein the oxygen delivery unit includes oxygen diluter cavities each oxygen diluter cavity disposed between an orifice and a port.

9. The device of claim 8, wherein the oxygen diluter cavities are configured to enable insertion of an oxygen tube connector into any one of the oxygen diluter cavities.

10. The device of claim 1, wherein the oxygen delivery unit includes ports where each of a plurality of oxygen diluter cavities is associated with one of the ports.

11. The device of claim 1, wherein oxygen concentrations provided by the device include 24% oxygen concentration, 28% oxygen concentration, 31% oxygen concentration, 35% oxygen concentration, 40% oxygen concentration, and 50% oxygen concentration.

12. The device of claim 11, wherein an oxygen delivery rate range of 2 liters per minute (LPM) to 4 LPM is associated with the 24% oxygen concentration. an oxygen deliver rate range of 4 LPM to 6 LPM is associated with the 28% oxygen concentration, an oxygen delivery rate range of 6 LPM to 8 LPM is associated with the 31% oxygen concentration, an oxygen delivery rate range of 8 LPM to 10 LPM is associated with the 35% oxygen concentration, an oxygen delivery rate range of 8 LPM to 12 LPM is associated with the 40% oxygen concentration, and an oxygen delivery rate of 12 LPM is associated with the 50% oxygen concentration.

13. The device of claim 1, wherein the oxygen concentrations provided by the device include 45% oxygen concentration.

14. The device of claim 13, wherein an oxygen delivery rate of 10 liters per minute (LPM) is associated with the 45% oxygen concentration.

15. The device of claim 1, further comprising windows, wherein the windows have a width that is between 0.635 inch and 0.675 inch and a height that is between 0.200 inches and 0.320 inch.

16. The device of claim 1, further comprising windows, wherein the windows have a width that is approximately 0.675 inch and a height that is approximately 0.200 inch.

17. The device of claim 1, wherein the oxygen delivery unit further comprises an inner and an outer chamber, wherein the inner chamber comprises openings for entraining room air received from the outer chamber with oxygen received by the oxygen delivery unit from an oxygen source.

18. The device of claim 17, wherein the size of the inner chamber openings are fixed.

19. The device of claim 17, wherein the inner chamber is configured to enable a first end of a tube to be coupled to the inner chamber and wherein the second end of the tube is configured to enable coupling with an oxygen mask.

20. The device of claim 17, wherein the oxygen delivery unit further comprises an outer chamber surrounding the inner chamber.

21. The device of claim 20, wherein the sizes of the outer chamber's two openings are fixed.

22. The device of claim 20, wherein the outer chamber has two openings, the opening providing a fluid passageway between the room air and the outer chamber.

23. The device of claim 22, wherein the inner chamber's openings and the outer chamber's openings are oriented with respect to each other along an imaginary straight line that goes through the center of the oxygen delivery unit.

24. The device of claim 20, wherein the outer chamber includes at least one side port.

25. The device of claim 24, wherein the side port is configured to enable an additional device to be coupled to the oxygen delivery unit.

26. The device of claim 25, wherein the additional device is selected from a group consisting of a second oxygen source, a nebulizer, and an air humidifier.

27. A method for delivering diluted oxygen to a patient, comprising:
providing a first port integral with a configurable oxygen delivery unit configured for decoupling a first end of an oxygen tube from the first port, wherein a second end of the oxygen tube is connected to a source of oxygen; and
providing a second port integral with the configurable oxygen delivery unit configured for coupling the first end of the oxygen tube with the second port, each port comprising an orifice, each orifice (i) forming a jet flow of oxygen entering the device, and (ii) having the size that pertains to a particular oxygen concentration, wherein the size of each orifice determines a velocity of oxygen, at a predetermined flow rate, entering the device through the respective orifice, and wherein the velocity of oxygen is selected to entrain room air to achieve a predetermined oxygen concentration within the device, wherein different oxygen concentrations are associated with the first and second ports and wherein the configurable oxygen delivery unit is structured to enable selectively altering the oxygen concentration within the device from a first concentration to a second concentration by fluidly coupling the first end of the oxygen tube with an orifice pertaining to a particular oxygen concentration.

28. The method as recited by claim 27, further comprising:
providing a first oxygen concentration by enabling insertion of the first end of the oxygen tube into the first port; and
providing a second oxygen concentration by enabling insertion of the first end of the oxygen tube into the second port.

29. The method as recited by claim 27, further comprising:
providing a first orifice for the first port;
providing a second orifice for the second port, wherein the first orifice and the second orifice have different sizes.

30. The method as recited by claim 29, further comprising:
providing a first cavity and a second cavity, wherein the first orifice and the first port are associated with the first cavity and the second orifice and the second port are associated with the second cavity and wherein the cavities are configured to enable insertion of the first end of the oxygen tube into each of the cavities.

31. The method as recited by claim 29, further comprising:
selecting sizes of the first orifice and the second orifice from a group of ranges consisting of 0.0100-0.0400 inch, 0.0200-0.0550 inch, 0.0400-0.0760 inch, 0.0550-0.1065 inch, 0.0760-0.1270 inch, 0.1065-0.1719 inch, and 0.1270-0.2000 inch.

32. The method as recited by claim 29, further comprising: selecting sizes of the first orifice and the second orifice from a group consisting of approximately 0.0200 inch, 0.0400 inch, 0.0550 inch, 0.0760 inch, :0.1065 inch, 0.1270 inch, and 0.1719 inch.

33. The method as recited by claim 29, further comprising: providing the first orifice with a size that is fixed; and providing the second orifice with a size that is fixed.

34. The method as recited by claim 27, wherein the method further comprises:
providing a chamber with openings for entraining room air with oxygen received from the oxygen source.

35. The method as recited by claim 34, wherein the providing of the chamber with the openings further comprises:
providing openings with fixed sizes.

36. The method as recited by claim 34, wherein the chamber is an inner chamber and wherein the method further comprises:
providing an outer chamber.

37. The method as recited by claim 36, wherein the method further comprises:
providing a side port in the outer chamber.

38. A device for delivering diluted oxygen to a patient, the device comprising:
a first-oxygen-concentration-delivery-component configured to deliver a first oxygen concentration to the patient; and
a second-oxygen-concentration-delivery-component configured to deliver a second oxygen concentration to the patient, each oxygen-concentration-delivery-component comprising an orifice, each orifice (i) forming a jet flow of oxygen entering the device, and (ii) having a size that pertains to a particular oxygen concentration, wherein the size of each orifice determines a velocity of oxygen, at a predetermined flow rate, entering the devise through the respective orifice, and wherein the velocity of oxygen is selected to entrain room air to achieve a predetermined oxygen concentration within the device, wherein the device is structured to enable selectively altering the oxygen concentration within the device from the first concentration to the second concentration by fluidly coupling an oxygen tube connector with an orifice pertaining to an particular oxygen concentration.

39. The device of claim 38, wherein the device is a first device and wherein the first device further comprises:
an additional-device-coupling-component configured to couple an additional device with the first device.

40. The device of claim 38, further comprising:
a humidified-air-receiving-component configured to receive humidified air.

41. The device of claim 38, further comprising:
a nebulized-medication-receiving-component configured to receive nebulized medication.

42. The device of claim 38, wherein the first-oxygen-concentration-delivery-component and the second-oxygen-concentration-delivery-component each include an oxygen-tube-connector-to-device-coupling-component configured to couple an oxygen tube connector to the device.

43. The device of claim 42, wherein each of the orifices is a different size.

44. The device of claim 42, wherein the size of each of the orifices is fixed.

45. The device of claim 42, wherein the orifices have sizes selected from a group of ranges consisting of 0.0100-0.0400 inch, 0.0200-0.0550 inch, 0.0400-0.0760 inch, 0.0550-0.1065 inch, 0.0760-0.1270 inch, 0.1065-0.1719 inch, and 0.1270-0.2000 inch.

46. The device of claim 45, wherein the orifices have sizes selected from a group consisting of approximately 0.0200 inch, 0.0400 inch, 0.0550 inch, 0.0760 inch, 0.1065 inch, 0.1270 inch, and 0.1719 inch.

47. The device of claim 42, wherein the orifice with the largest size is located in the center of the device and the orifices with smaller sizes are located around the largest sized orifice.

48. The device of claim 38, further comprising:
a room-air-entrainment-component configured to entrain room air into oxygen that the device receives from an oxygen source.

49. The device of claim 48, wherein the room-air-entrainment-component includes air entrainment windows that each have a fixed size.

50. The device of claim 49, further comprising:
an air-entrainment-windows-occlusion-prevention-component surrounding the room-air-entrainment-component, the air-entrainment-windows-occlusion-prevention-component configured to prevent occlusion of the air entrainment windows.

51. The device of claim 50, further comprising;
a room-air-entrance-component configured to allow room air to enter the air-entrainment-windows-occlusion-prevention-component.

* * * * *